United States Patent
Fryszkowska et al.

(10) Patent No.: US 9,879,045 B2
(45) Date of Patent: Jan. 30, 2018

(54) PROCESSES FOR THE PREPARATION OF DEHYDROEPIANDROSTERONE AND ITS INTERMEDIATES

(71) Applicant: DR. REDDY'S LABORATORIES LIMITED, Hyderabad (IN)

(72) Inventors: Anna Fryszkowska, Cambridge (GB); Michael Siegfried Quirmbach, Basel (CH); Srikanth Sarat Chandra Gorantla, Hyderabad (IN); Sanjay Reddy Alieti, Hyderabad (IN); Srinivas Reddy Poreddy, Nalgonda (IN); Naresh Kumar Reddy Dinne, Mahaboob Nagsar (IN); Upadhya Timmanna, Hyderabad (IN); Vilas Dahanukar, Hyderabad (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 52 days.

(21) Appl. No.: 14/892,539

(22) PCT Filed: May 21, 2014

(86) PCT No.: PCT/IB2014/061590
§ 371 (c)(1),
(2) Date: Nov. 19, 2015

(87) PCT Pub. No.: WO2014/188353
PCT Pub. Date: Nov. 27, 2014

(65) Prior Publication Data
US 2016/0122382 A1    May 5, 2016

(30) Foreign Application Priority Data
May 21, 2013 (IN) .......................... 2214/CHE/2013

(51) Int. Cl.
| C12P 33/00 | (2006.01) |
| C12P 1/00 | (2006.01) |
| C12P 7/02 | (2006.01) |
| C12P 7/22 | (2006.01) |
| C07J 1/00 | (2006.01) |

(52) U.S. Cl.
CPC ............. *C07J 1/0011* (2013.01); *C12P 33/00* (2013.01)

(58) Field of Classification Search
None
See application file for complete search history.

(56) References Cited

U.S. PATENT DOCUMENTS

| 2,186,906 | A | 1/1940 | Mamoli |
| 4,791,057 | A | 12/1988 | Misaki et al. |
| 5,604,213 | A | 2/1997 | Barrie et al. |
| 6,284,750 | B1 | 9/2001 | Gubernick et al. |
| 8,227,208 | B2 | 7/2012 | Gupta et al. |

FOREIGN PATENT DOCUMENTS

| CN | 101362789 A | 2/2009 |
| CN | 101717422 A | 6/2010 |
| CN | 102212099 A | 10/2011 |
| CN | 102603839 A | 7/2012 |
| CN | 102603841 A | 7/2012 |
| EP | 0133995 A2 | 3/1985 |
| KR | 1020040040555 A | 5/2004 |

OTHER PUBLICATIONS

International Search Report for corresponding International Patent Application No. PCT/IB2014/061590, dated Nov. 28, 2014.
International Preliminary Report on Patentability for corresponding International Patent Application No. PCT/IB2014/061590, dated Nov. 24, 2015.
Jones and Wigfield, "Steroids and steroidases. VI. On the C-17 specificity of the 5-3-ketoisomerase of Pseudomonas testosteroni and evidence for substrate micelle formation", Canadian Journal of Chemistry, May 1, 1968, pp. 1459-1465, vol. 46-issue No. 9, The National Research Council of Canada.
Bawa et al., "Enzymatic Reduction of Ketones to Optically Active Secondary Alcohols", Journal of Physical Science, 2008, pp. 1-5, vol. 19-Issue No. 2.
Hamid et at., "Aldo-keto Reductase Family 1 Member C3 (AKR1C3) is a Biomarker and Therapeutic Target for Castration-Resistant Prostate Cancer", Molecular Medicine, Jan. 22, 2013, pp. 1449-1455, vol. 18.
Written Opinion for corresponding International Patent Application No. PCT/IB2014/061590, dated Nov. 28, 2014.
Daniel L. Purich and R. Donald Allison, The Enzyme Reference: A Comprehensive Guidebook to Enzyme Nomenclature, Reactions, and Methods, Dec. 2002, pp. 782 and 783.
Copeland et al., "Sphingomonas wittichii RW1, complete genome", GenBank: CP000699.1, Nucleotide—NCBI, pp. 1 to 797.

*Primary Examiner* — Thomas J Visone
(74) *Attorney, Agent, or Firm* — Pergament & Cepeda LLP; Milagros A. Cepeda; Edward D. Pergament

(57) ABSTRACT

The present application relates to a regioselective and stereoselective processes for the preparation of dehydroepiandrosterone (DHEA) and processes for its intermediates.

5 Claims, No Drawings

PROCESSES FOR THE PREPARATION OF DEHYDROEPIANDROSTERONE AND ITS INTERMEDIATES

This application is a National Stage Application under 35 U.S.C. §371 of PCT International Application No. PCT/IB2014/061590, filed May 21, 2014, which claims the benefit of Indian Provisional Application No. 2214/CHE/2013, filed May 21, 2013, all of which are hereby incorporated by reference in their entireties.

INTRODUCTION

The present application relates to a regioselective and stereoselective processes for the preparation of dehydroepiandrosterone (DHEA) and processes for its intermediates.

BACKGROUND OF THE INVENTION

Dehydroepiandrosterone (DHEA) also known as androstenolone or prasterone or 3β-hydroxyandrost-5-en-17-one or 5-androsten-3β-ol-17-one, is an important endogenous steroid hormone and has the structure of formula (I).

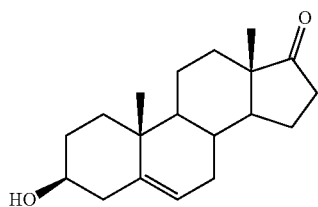
(I)

Dehydroepiandrosterone (DHEA) is a key intermediate in the synthesis of steroidal molecules, including but not limited to abiraterone acetate, a drug used in the treatment of castration-resistant prostate cancer.

An article by J. Bryan Jones et al., "Steroids and steroidases.VI. On the C-17 specificity of the Δ5-3-ketoisomerase of Psudomonas testosterone and evidence for substrate micelle formation," Candian Journal of Chemistry, 46,1459-1465 (1968) describes a process for the preparation of androst-5-ene-3,17-dione, an intermediate used for the preparation of DHEA. The process disclosed in the said reference involves reacting androst-4-ene-3,17-dione with potassium t-butoxide in t-butyl alcohol under nitrogen atmosphere for 90 minutes at 20° C., followed by quenching the reaction mass by rapid addition of 10% aqueous acetic acid, adding excess sodium bicarbonate, extracting with ether, evaporating at room temperature and recrystallization from acetone to give androst-5-ene-3,17-dione.

However, the above process is disadvantageous in that, it involves the use of higher amounts of base i.e., 10 equivalents of potassium tert-butoxide, results in the formation of oxidized impurities of androst-5-ene-3,17-dione and has workup procedure which may not suitable on an industrial scale and thereby results in low and unsatisfactory yields.

Accordingly, there remains a need to provide improved processes for preparing androst-5-ene-3,17-dione that eliminates and reduces the drawbacks of the prior art in a convenient manner.

Chinese Patent Application Publication No. 102212099 disclose a multi-step process for the preparation of dehydroepiandrosterone starting from 16-dehydropregnenolone acetate and involves the reaction steps as depicted in Scheme 1 below.

Scheme 1

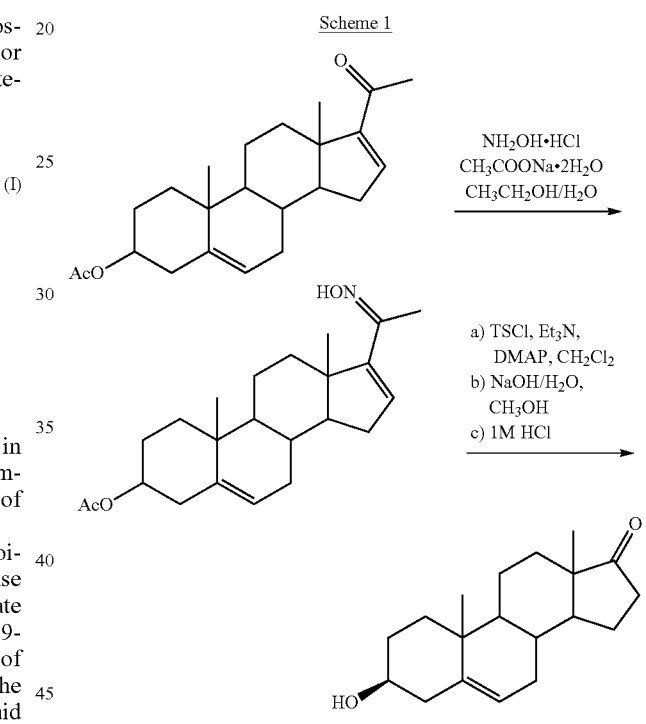

Chinese Patent Application Publication No. 102603841 disclose a multi-step process for the preparation of dehydroepiandrosterone from 4-androsten-3,17-dione, and involves the reaction steps as depicted in Scheme 2 below.

Scheme 2

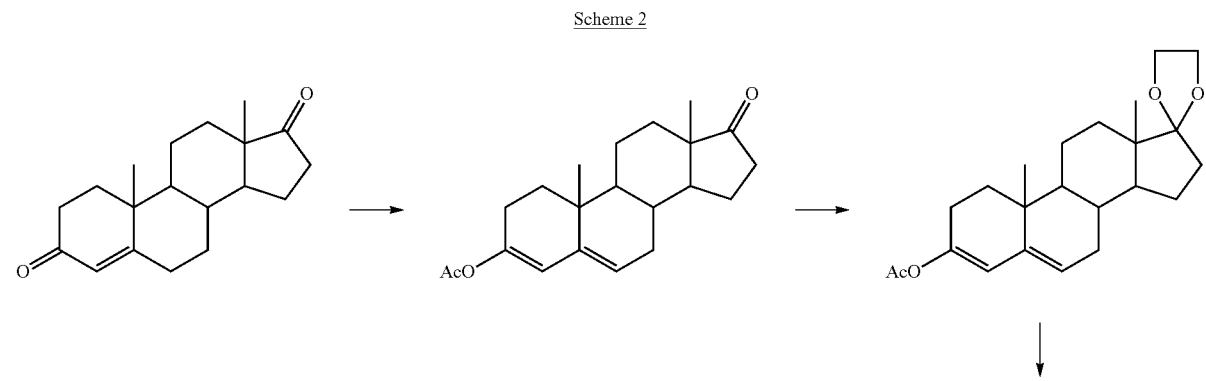

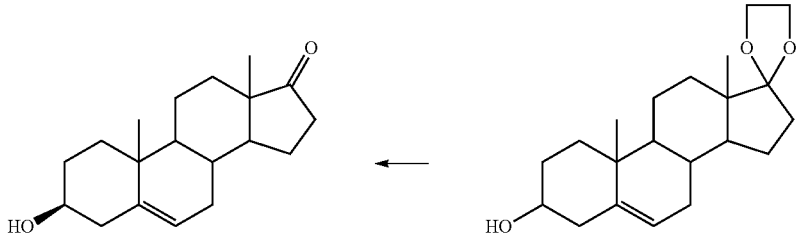

Chinese Patent Application Publication No. 102603839 describes a multi-step synthetic process for preparation of dehydroepiandrosterone starting from 16-dehydropregnenolone acetate, which involves (i) preparation of 16-dehydropregnenolone acetate oxime (ii) Beckmann rearrangement of 16-dehydropregnenolone acetate oxime to obtain dehydroepiandrosterone acetate (iii) hydrolysis of dehydroepiandrosterone acetate to give dehydroepiandrosterone. The reaction steps of the said process are depicted in Scheme 3 below.

is a 3β-hydroxysteroid or a 3-ketosteroid) in a specimen to be assayed, which involves the steps of causing this component in the specimen to take part in the 3β-hydroxysteroid & 3-ketosteroid cycling reaction and measuring a detectable change in the reaction system comprising a 3β-hydroxysteroid oxidase and or 3β-hydroxysteroid dehydrogenase. In the cycling reaction, 3β-hydroxysteroid oxidase consumes $O_2$ and converts 3-hydroxy steroid to a 3-ketosteroid, 3β-hydroxysteroid dehydrogenase in the presence of reduced $NAD(P)^+$ converts 3-ketosteroid to a 3-hydroxy steroid and Scheme 3

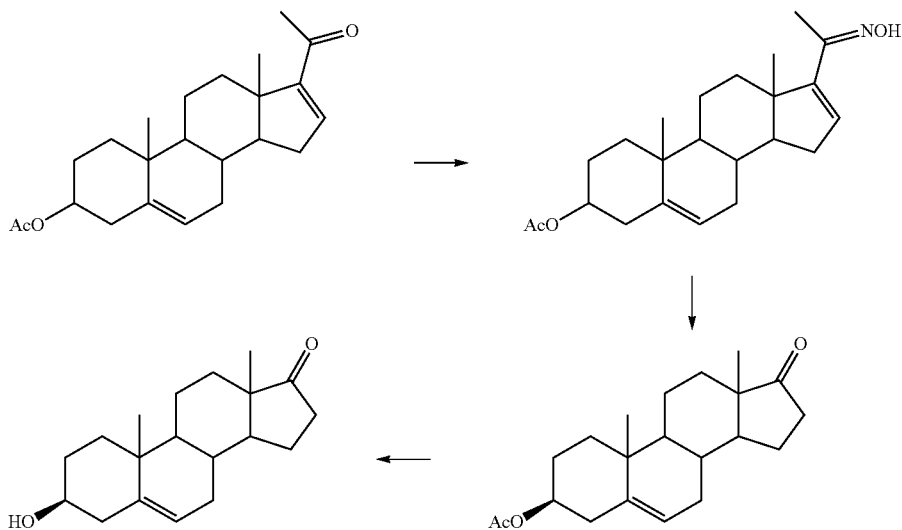

Chinese Patent Application Publication No. CN 101362789 and 101717422, Korean patent application Publication No. 2004040555 also discloses synthetic processes for the preparation of dehydroepiandrosterone.

The above described synthetic processes for the preparation of dehydroepiandrosterone includes multiple steps, and a sequence of protection/deprotection steps in order to achieve a stereo- and regioselective reduction at position C3 and may not be suitable for commercial scale synthesis.

Mamoli et al., in U.S. Pat. No. 2,186,906 describes biochemical hydrogenation process for the conversion of a keto-compound of the cyclopentano-10,13-dimethyl-polyhydro-phenanthrene series ($\Delta^{4,5}$-androstendione) into a corresponding hydroxyl compound of the same series ($\Delta^{4,5}$-androstenole-17-one-3) which comprises subjecting such keto compound to the action of a reducing yeast-containing fermentation solution.

Misaki et al., in U.S. Pat. No. 4,791,057 describes highly sensitive quantitative assay method for a component (which generate NAD(P). The 3β-hydroxysteroid & 3-ketosteroid cycling reaction described in the said patent is schematically represented in Scheme 4 below:

Scheme 4

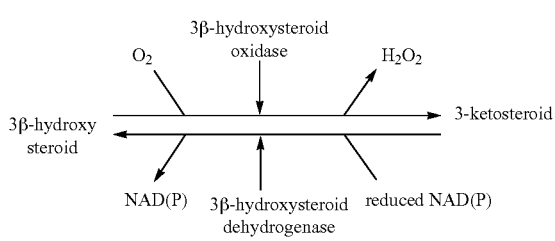

Though the above references discloses a enzymatic conversion of 3-hydroxy steroid to 3-keto steroids or vice-versa, they do not disclose a process for the preparation of dehydroepiandrosterone and there remains a complex challenge in developing an improved process which displays required regioselectivity by reducing the 3-oxo group of the steroid leaving the 17-oxo group intact and stereoselectivity by producing the corresponding 3β-hydroxy compound.

The process according to the present application relates to an enzymatic process for the preparation of dehydroepiandrosterone. The enzymatic reduction process of the present application is eco-friendly, cost-effective and commercially viable.

SUMMARY OF THE INVENTION

In an aspect, the present application provides a process for preparing 3β-hydroxyandrost-5-en-17-one of formula (I)

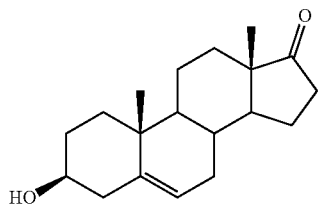

(I)

comprising regioselectively and stereoselectively reducing the 3-oxo group of $\Delta^5$-androstene-3,17-dione of formula (II)

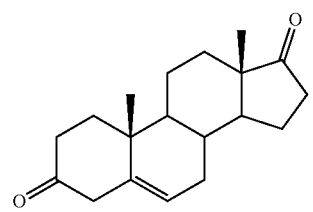

(II)

using a ketoreductase enzyme.

In another aspect, the present application provides a process for the preparing a 3β-hydroxyandrost-5-en-17-one of formula (I)

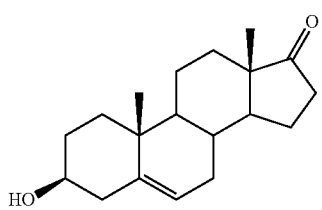

(I)

comprising reducing 3-oxo group of $\Delta^5$-androstene-3,17-dione of formula (II)

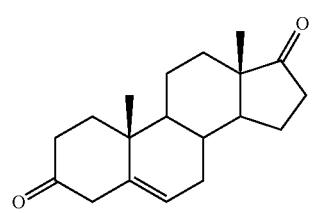

(II)

using a ketoreductase enzyme having Sequence ID No:1.

In an aspect, the present application provides a process for the preparing $\Delta^5$-androstene-3,17-dione of formula (II)

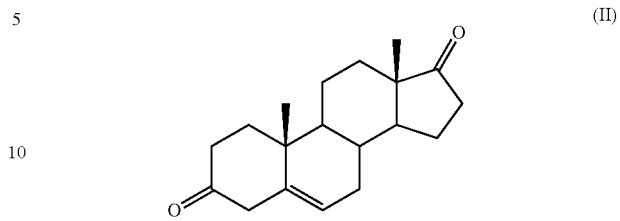

(II)

comprising the steps of:
a) isomerizing $\Delta^4$-androstene-3,17-dione of formula (IV)

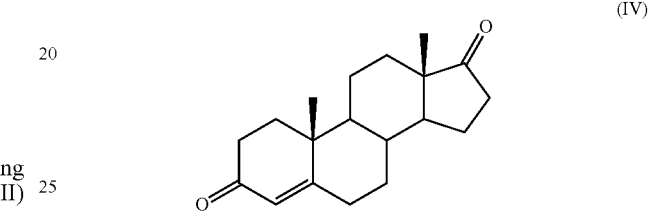

(IV)

using potassium tertiary butoxide and tertiary butanol to provide $\Delta^5$-androstene-3,17-dione of formula (II);

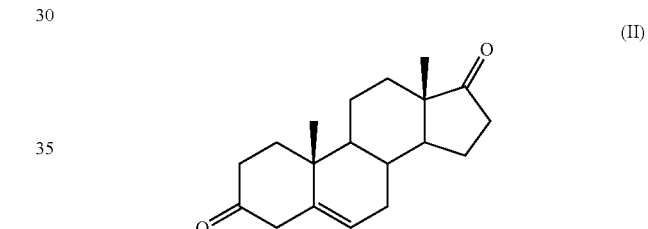

(II)

b) recrystallizing the compound of formula (II) from a halogenated hydrocarbon.

In another aspect, the present application provides a process for the preparing $\Delta^5$-androstene-3,17-dione of formula (II)

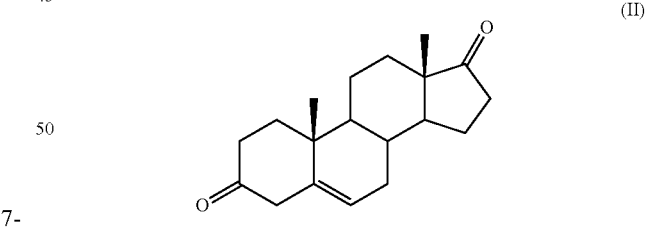

(II)

comprising the steps of:
a) isomerizing $\Delta^4$-androstene-3,17-dione of formula (IV)

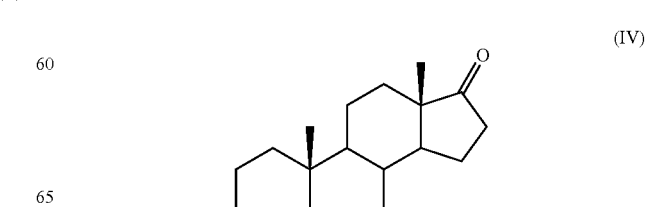

(IV)

using potassium tertiary butoxide and tertiary butanol to provide Δ⁵-androstene-3,17-dione of formula (II);

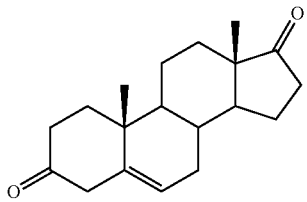
(II)

b) isolating the compound of formula (II) in the presence of an antioxidant.

DETAILED DESCRIPTION

In an aspect, the present application provides a process for preparing 3β-hydroxyandrost-5-en-17-one of formula (I)

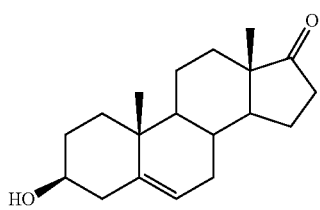
(I)

comprising regioselectively and stereoselectively reducing the 3-oxo group of Δ⁵-androstene-3,17-dione of formula (II)

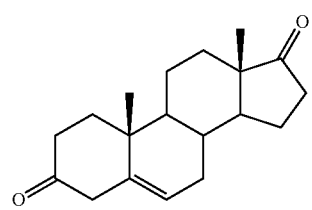
(II)

using a ketoreductase enzyme.

The compound of formula (II) may be obtained by the processes known in the art or by the processes disclosed in the present application.

The regioselective and stereoselective reduction of the compound of formula (II) is carried out in the presence of ketoreductase enzyme and the reaction system further comprises a co-factor, a co-factor regeneration system, a substrate and dehydrogenase enzyme, a buffer solution and an organic solvent.

"Stereoselective or Stereoselectivity" as used herein refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly reported in the art (typically as a percentage) as the enantiomeric excess calculated therefrom according to the formula [major enantiomer−minor enantiomer]/[major enantiomer+ minor enantiomer]. Where the stereoisomers are diastereoisomers, the stereoselectivity is referred to as diastereoselectivity, the fraction (typically reported as a percentage) of one diastereomer in the sum with others. In the context of the present disclosure, stereoselectivity refers to the fraction (typically reported as a percentage) of the 3β-hydroxy compound of formula (I), as opposed to the 3α-hydroxy compound of formula (I).

"Regioselective or Regioselectivity" as used herein refers to the preference of one direction of chemical bond making or breaking over all other possible directions, or the preference for the formation of one product over another. In the context of the present disclosure, regioselectivity refers to the preferential reduction of the 3-oxo group over 17-oxo group or both 3-oxo and 17-oxo groups of the compound of formula (II). In an embodiment, regioselectivity in the context of the present disclosure refers to the preferential reduction of the 3-oxo group of the compound of formula (II) in an order of greater than 90 wt %, preferably greater than 95 wt %, more preferably greater than 97wt %, more preferably greater than 99 wt %, corresponding to the input weight compound of formula (II).

The "ketoreductase enzyme" refers to an enzyme that catalyzes the reduction of a ketone or aldehyde to form the corresponding alcohol. The reaction may be carried out in the presence of the co-factor (NAD(P)⁺ or NAD(P)H), optionally with the aid of co-factor recycling system. Ketoreductase enzymes include, for example, those classified under the EC numbers of 1.1.1. Such enzymes are given various names in addition to ketoreductase, including, but not limited to, alcohol dehydrogenase, carbonyl reductase, lactate dehydrogenase, hydroxyacid dehydrogenase, hydroxyisocaproate dehydrogenase, β-hydroxybutyrate dehydrogenase, steroid dehydrogenase, sorbitol dehydrogenase, hydroxysteroid oxidase, ketosteroid reductase, aldoketoreductase (AKR) and aldoreductase. NADPH-dependent ketoreductases are classified under the EC number of 1.1.1.2 and the CAS number of 9028-12-0. NADH-dependent ketoreductases are classified under the EC number of 1.1.1.1 and the CAS number of 9031-72-5.

The ketoreductase enzyme can be a wild-type or a recombinant enzyme, used either as whole cells or in the isolated/semi-purified form. Preferably, the ketoreductase is isolated. The ketoreductase can be separated from any host, such as mammals, filamentous fungi, yeasts, and bacteria.

In another embodiment, ketoreductase enzymes include those enzymes obtained from *Sphingomonas wittichii* (strain RW1/DSM 6014/JCM 10273) A5VBG8).

In another embodiment, ketoreductase enzymes used for the above described stereoselective reduction include, but not limited to, enzyme having a amino acid sequence that corresponds to Sequence ID No:1. As used herein the enzyme having Sequence ID No:1 corresponds to Sequence ID No:1 or is at least about 80%, 81%, 82%, 83%, 84%, 85%, 86%, 87%, 88%, 89%, 90%, 91%, 92%, 93%, 94%, 95%, 96%, 97%, 98% or 99% identical to Sequence ID No:1.

The ketoreductase enzyme can be an enzyme having Sequence ID No. 1 or equivalent products thereof. As used herein, the term "equivalent" refers to an enzyme or product with similar to identical enzymatic activity.

In an embodiment, ketoreductase enzymes include a cofactor dependent ketoreductases.

According to the process of the present application, the co-factor may be selected from the group consisting of NADH, NADPH, NAD⁺, NADP⁺, salts thereof, and mixtures thereof. Preferably, when the ketoreductase is NADH-dependent, the co-factor is selected from the group consisting of NADH, NAD$^+$, salts thereof, and mixtures thereof. More preferably, the co-factor is NADH or a salt thereof. Preferably, when the ketoreductase is NADPH-dependent, the co-factor is selected from the group consisting of NADPH, NADP$^+$, salts thereof, and mixtures thereof. More preferably, the co-factor is NADPH or a salt thereof. Examples of salts of the co-factors include NAD tetra (cyclohexyl ammonium) salt, NAD tetrasodium salt, NAD$^+$ tetrasodium hydrate, NADP$^+$ phosphate hydrate, NADP$^+$ phosphate sodium salt, and NADH dipotassium salt.

According to the process of the present application, the co-factor regeneration system comprises a set of reactants that participate in a reaction and reduces the oxidized form of the cofactor (e.g., NADP$^+$ to NADPH). Cofactors oxidized by the ketoreductase-catalyzed reduction of the compound of formula (II) are regenerated in reduced form by the cofactor regeneration system. For example, a co-factor regeneration system comprises a substrate which is a source of reducing hydrogen equivalents and is capable of reducing the oxidized form of the cofactor and a catalyst, for example an enzyme catalyst, that catalyzes the reduction of the oxidized form of the cofactor by the reductant.

Preferably, the co-factor regeneration system comprises a substrate/dehydrogenase enzyme pair selected from the group consisting of D-glucose/glucose dehydrogenase, sodium formate/formate dehydrogenase, lactate/lactate dehydrogenase and phosphite/phosphite dehydrogenase.

In an embodiment, D-glucose/glucose dehydrogenase pair is used. Glucose dehydrogenase (GDH) includes, for example, those classified under the EC number 1.1.1.47 and are commercially available, for example, from Codexis, Inc. under the catalog number GDH-CDX-901.

For example, when the glucose/glucose dehydrogenase cofactor regeneration system is employed, the co-production of gluconic acid (pKa=3.6), causes the pH of the reaction mixture to drop if the resulting aqueous gluconic acid is not otherwise neutralized. The pH of the reaction mixture may be maintained at the desired level by standard buffering techniques, wherein the buffer neutralizes the gluconic acid up to the buffering capacity provided, or by the addition of a base concurrent with the course of the conversion.

The reduction reaction may be carried out in the presence of a buffer having a pH of from about 4 to about 9, more preferably from about 4 to about 8, more preferably from about 5 to about 8, most preferably from about 6 to about 8 or about 5 to about 7. Preferably, the buffer is a solution of a salt. Preferably, the salt is selected from the group consisting of potassium phosphate or TRIS-salt, magnesium sulfate, and mixtures thereof. Optionally, the buffer comprises a thiol compound.

The reduction reaction may be carried out at a temperature of about 10° C. to about 50° C. Preferably, the process is carried out at ambient temperature, at a temperature of about 20° C. to about 40° C., or about 25° C. to about 35° C.

The reduction reaction may be carried out in the presence of a water miscible or water immiscible organic solvent and may be selected from alcohol such as t-butanol, esters such as ethylacetate, isopropyl acetate, or the like, ethers such as tetrahydrofuran, methyl tetrahydrofuran, methyl tert-butyl ether or the like, aromatic hydrocarbons such as toluene and polar aprotic solvents such as dimethylformamide, dimethylsulfoxide or the like.

In an embodiment, a water immiscible organic solvent is used. In a preferred embodiment, a water immiscible organic solvent in the ratio of 2-98%, v/v, more preferably 25-75%, v/v with respect to water is used.

In an embodiment, the reduction of the 3-oxo group of $\Delta^5$-androstene-3,17-dione of formula (II) is carried out with a substrate (Formula II) concentration in the range of 0.1-500 g/L, preferably at least 50-300 g/L.

In another embodiment, the reduction of the 3-oxo group of $\Delta^5$-androstene-3,17-dione of formula (II) is carried out in the presence of ketoreductase enzyme having Sequence ID No:1.

In an embodiment, the reduction of the 3-oxo group of $\Delta^5$-androstene-3,17-dione of formula (II) is carried out with enzyme loading in the range 0.1-20 weight % with respect to substrate, but preferably less than 10 weight % with respect to substrate i.e., Formula (II).

In another embodiment, the reduction of the 3-oxo group of $\Delta^5$-androstene-3,17-dione of formula (II) is carried out in the presence of potassium phospate buffer of pH 6.5 and ionic strength 50 mM, In yet another embodiment, the reduction of the 3-oxo group of $\Delta^5$-androstene-3,17-dione of formula (II) is carried out in the presence of co-factor NAD$^+$, NAD(P)$^+$, co-factor regeneration system comprising glucose and glucosedehydrogenase (GDH-CDX-901).

In an embodiment, the reduction of the 3-oxo group of $\Delta^5$-androstene-3,17-dione of formula (II) is carried out in the presence of organic solvent selected from ethyl acetate, isopropyl acetate, tetrahydrofuran, methyl tetrahydrofuran, methyl tert-butyl ether, toluene, dimethylformamide or dimethyl sulfoxide.

In an embodiment, the reduction of the 3-oxo group of $\Delta^5$-androstene-3,17-dione of formula (II) is carried out at a temperature of about 25° C. to about 35° C.

In a preferred embodiment, the reduction of the 3-oxo group of $\Delta^5$-androstene-3,17-dione of formula (II) is carried out in the presence of enzyme of Sequence ID No.1. ketoreductase enzyme, potassium phospate buffer of pH 6.5 and ionic strength 50 mM, co-factor NAD$^+$, NAD(P)$^+$, co-factor regeneration system comprising glucose and glucosedehydrogenase (GDH-CDX-901).

The inventors of the present application have surprisingly found that the process described herein is highly regiospecific in that it selectively reduces the 3-oxo group over 17-oxo group of $\Delta^5$-androstene-3,17-dione of formula (II) and is also stereospecific in that 3-oxo group of $\Delta^5$-androstene-3,17-dione of formula (II) is selectively reduced to provide the corresponding 3β-hydroxy compound.

Further, the process of the present application is advantageous in that it is selective, green, quantitative and avoids using protection/deprotection steps, as well as avoids the use of toxic oxidative reagents, performed under mild conditions (temperature, pH), high substrate concentrations and is an efficient and straightforward route to DHEA and its derivatives, Further, the process of the present application is advantageous in that it provides yields in the range of 80% to 99%, and with a degree of stereo-selectivity of greater than 95%, preferably greater than 99%, more preferably 99.5%.

In another aspect, the present application provides a process for the preparing a 3β-hydrooxyandrost-5-en-17-one of formula (I)

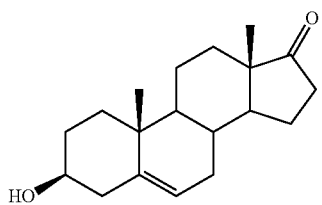

(I)

comprising reducing 3-oxo group of Δ⁵-androstene-3,17-dione of formula (II)

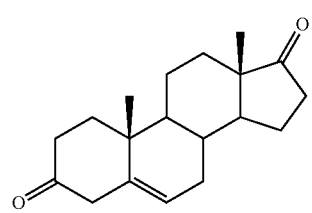

(II)

using a ketoreductase enzyme having Sequence ID No:1.

The process of reducing 3-oxo group of Δ⁵-androstene-3,17-dione of formula (II) using a ketoreductase enzyme having Sequence ID No:1 may be carried out according to the procedures disclosed above or according to the process described in the examples.

In an embodiment, the present application provides a process comprising the steps of converting the compound of formula (I) obtained by a process as described above to a compound of formula (III).

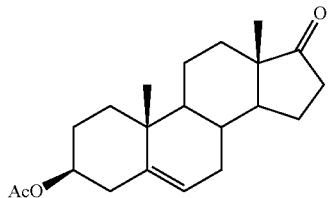

(III)

In another embodiment, the present application provides a process for the preparing a compound of formula (III)

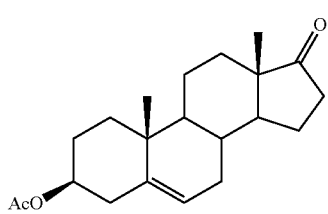

(III)

comprising the steps of:
a) regioselectively and stereoselectively reducing the 3-oxo group of Δ⁵-androstene-3,17-dione of formula (II)

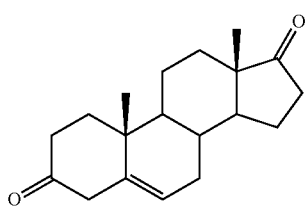

(II)

using a ketoreductase enzyme to obtain 3β-hydroxyandrost-5-en-17-one of formula (I);

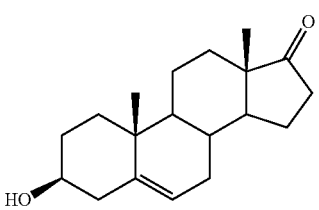

(I)

b) converting the compound of formula (I) to a compound of formula (III).

The compound of formula (I) may be converted to the compound of formula (III) by the processes known in the art or by the processes disclosed in the present application.

In an aspect, the present application provides a process for the preparing Δ⁵-androstene-3,17-dione of formula (II)

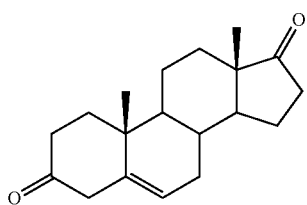

(II)

comprising the steps of:

a) isomerizing Δ⁴-androstene-3,17-dione of formula (IV)

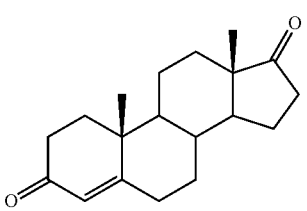

(IV)

using potassium tertiary butoxide and tertiary butanol to provide Δ⁵-androstene-3,17-dione of formula (II);

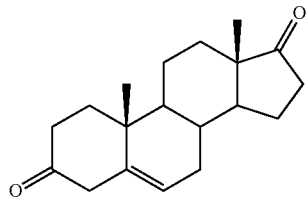
(II)

b) recrystallizing the compound of formula (II) from a halogenated hydrocarbon.

The reaction of step a) may be carried out at a temperature of about 10° C. to about 50° C. Preferably, at a temperature of about 20° C. to about 40° C. or at about 25° C. to about 35° C.

In an embodiment, after the completion of the reaction, the reaction mixture comprising $\Delta^5$-androstene-3,17-dione of formula (II) is quenched using acetic acid, preferably using 10% acetic acid and pH of the reaction mixture is adjusted to about 6.0 to about 7.5 using a inorganic base, preferably using sodium bicarbonate and isolating the compound of formula (II) by adding water.

The inventors of the present application have surprisingly found that recrystallizing the compound of formula (II) from a halogenated hydrocarbon solvent result in the compound of formula (II) with higher degree of yield and purity.

Halogenated hydrocarbon that may be used in step b) may be selected from dichloromethane, 1,2-dichloroethene, Carbon tetrachloride, chloroform, 1,1,1-trichloroethane or mixture thereof.

In another aspect, the present application provides a process for the preparing $\Delta^5$-androstene-3,17-dione of formula (II)

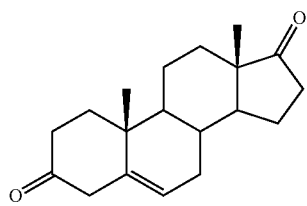
(II)

comprising the steps of:
a) isomerizing $\Delta^4$-androstene-3,17-dione of formula (IV)

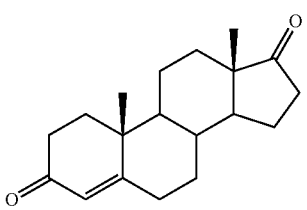
(IV)

using potassium tertiary butoxide and tertiary butanol to provide $\Delta^5$-androstene-3,17-dione of formula (II);

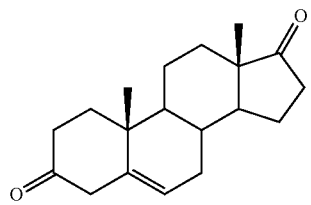
(II)

b) isolating the compound of formula (II) in the presence of an antioxidant.

The reaction of step a) may be carried out at a temperature of about 10° C. to about 50 C. Preferably, at a temperature of about 20° C. to about 40° C. or at about 25° C. to about 35° C.

The inventors of the present application have surprisingly found that isolating the compound of formula (II) in the presence of an anti-oxidant results in the compound of formula (II) with higher degree of yield, purity and with reduced or non-detectable quantities of the oxidized impurities formed during the reaction and thereby avoiding additional purification.

Anti-oxidant used in step b) may be selected from the group consisting of ascorbic acid, sodium ascorbate, calcium ascorbate, ascorbic palmitate, butylated hydroxylanisole, butylated hydroxytoluene, 2,4,5-trihydroxybutyrophenone, 4-hydroxymethyl-2,6-di-tert-butylphenol, erythorbic acid, propyl gallate, thiodipropionic acid, dilauryl thiodipropionate, tert-butylhydroquinone, tocopherols or mixtures thereof. In an embodiment, sodium ascorbate is used.

The amount of antioxidant used may be a catalytic amount for e.g., in the range of about 0.1 to about 0.5 equivalent per molar equivalent of formula (IV).

In an embodiment, the reaction mixture comprising the compound of formula (II) obtained in step a) may be added to the anti-oxidant mixture comprising acetic acid, water and the antioxidant selected.

In an embodiment, the present application provides a process for the preparing a compound of formula (III)

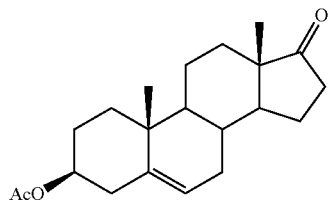
(III)

comprising the steps of:
a) isomerizing $\Delta^4$-androstene-3,17-dione of formula (IV)

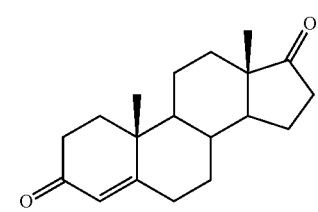
(IV)

to give Δ⁵-androstene-3,17-dione of formula (II);

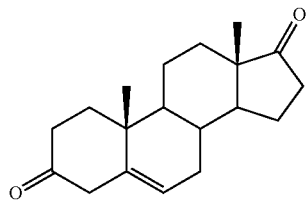
(II)

b) regioselectively and stereoselectively reducing the 3-oxo group of Δ⁵-androstene-3,17-dione of formula (II) using a ketoreductase enzyme to obtain 3β-hydroxyandrost-5-en-17-one of formula (I);

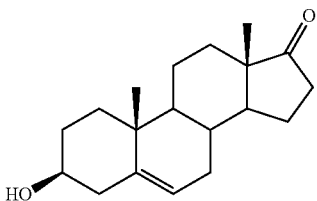
(I)

c) converting the compound of formula (I) to a compound of formula (III).

In another embodiment, the present application provides a process for the preparing a compound of formula (III)

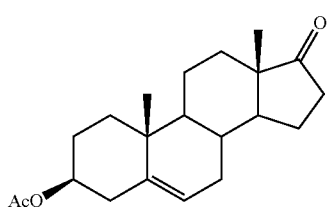
(III)

comprising the steps of:
a) isomerizing Δ⁴-androstene-3,17-dione of formula (IV)

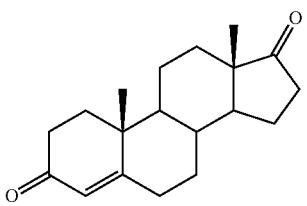
(IV)

to give Δ⁵-androstene-3,17-dione of formula (II);

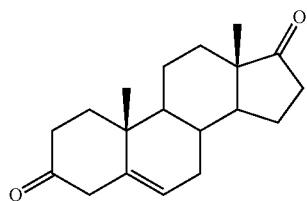
(II)

b) regioselectively and stereoselectively reducing the 3-oxo group of Δ⁵-androstene-3,17-dione of formula (II) using a ketoreductase enzyme having Sequence ID No:1 to obtain 3β-hydroxyandrost-5-en-17-one of formula (I);

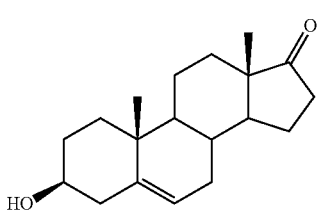
(I)

c) converting the compound of formula (I) to a compound of formula (III).

The acetylation may be carried in a manner know in the art. The acetylating agents that may be used include but not limited to acetyl chloride, acetic anhydride, methyl ortho formate or an equivalent acetylating agent. The solvents that may be used include but not limited to tetrahydrofuran, dichloromethane, toluene, chloroform, carbon tetrachloride, acetonitrile, N,N-dimethylformamide or combination thereof. The base that may be used include but not limited to diisopropylamine, dimethylamine, ethylenediamine, N,N-diisopropylmethylamine, 4-dimethylaminopyridine, N,N-diisopropylethylamine, triethylamine, aniline, pyridine, piperidine, and the like; and inorganic bases such as alkali metal or alkaline earth metal carbonates, hydrogen carbonates, hydroxides and oxides, for example, potassium carbonate, potassium hydrogen carbonate, potassium hydroxide, potassium acetate, potassium methoxide, sodium carbonate, sodium hydrogen carbonate, sodium hydroxide, sodium acetate, sodium methoxide, lithium carbonate, lithium hydrogen carbonate, lithium hydroxide, lithium acetate, lithium methoxide, barium hydroxide, calcium oxide, and the like.

In an embodiment, the dehydroepiandrosterone obtained above may further be converted to abiraterone acetate and DHEA Enanthate by methods known in the art.

Certain specific aspects and embodiments of the invention will be explained in more detail with reference to the following examples, which are provided for purposes of illustration only and should not be construed as limiting the scope of the invention in any manner.

EXAMPLES

Example 1

Preparation of 5-Androsten-3,17-dione

Tertiary butanol (75 mL) is charged into a round bottom flask at 25-30° C. under nitrogen atmosphere and stirred under nitrogen gas bubbling for 10 minutes. Potassium tertiary butoxide (9.79 g) is charged and stirred under nitrogen atmosphere at 30-35° C. for 10-15 minutes. 4-Androsten-3,17-dione (10.0 g) is charged to the round bottom flask at 30-35° C. and maintained at the same temperature for about 90 minutes. Acetic acid (5.75 g), water (200 mL) and sodium ascorbate (3.5 g) are charged into a second round bottom flask and stirred at 20-25° C. The obtained reaction mixture above is added to second round bottom flask and stirred at 20-25° C. for about 30 minutes. The product obtained is filtered, washed with water (100 mL) and dried under vacuum.

Yield: 90.5%

Purity by HPLC: 93.6%

Example 2

Preparation of 5-Androsten-3,17-dione

Tertiary butanol (2000 mL) is charged into a round bottom flask under nitrogen gas atmosphere at 25-30° C. and stirred under nitrogen gas bubbling for 10 minutes. Potassium tertiary butoxide (313.4 g) is charged and stirred under nitrogen gas bubbling at 35-40° C. for 10-15 minutes. 4-Androsten-3,17-dione (80.0 g) is charged into the round bottom flask at 35-40° C. and the reaction mixture is stirred under nitrogen gas bubbling at the same temperature for about 90 minutes. The reaction mixture is combined with 10% aqueous acetic acid solution (3130 mL) at 20-25° C. and reaction mixture pH is adjusted to 6.5 to 7.0 using sodium bicarbonate (200 g). Water (2500 mL) is added to the above reaction mixture and stirred for about 30 minutes. The solid obtained is filtered, washed with water (1000 mL) and suction dried. The product obtained is dissolved in dichloromethane (500 mL), the aqueous layer is separated and the organic layer is distilled completely under vacuum to give 5-androsten-3,17-dione.

Yield: 81.8%

Purity by HPLC: 92.30%

Example 3

Preparation of 5-Androsten-3,17-dione

Tertiary butanol (1500 mL) is charged into a round bottom flask under nitrogen gas atmosphere at 25-30° C. and stirred under nitrogen gas bubbling for 10 minutes. Potassium tertiary butoxide (235 g) is charged and stirred under nitrogen gas bubbling at 35-40° C. for 10-15 minutes. 4-Androsten-3,17-dione (60.0 g) is charged into the round bottom flask at 35-40° C. under nitrogen atmosphere and the reaction mixture is stirred under nitrogen gas bubbling at the same temperature for about 90 minutes. The reaction mixture was added to the 10% aqueous acetic acid solution (2500 mL) at 20-25° C. and stirred for 10-15 minutes. Water (1000 mL) is added to the above reaction mixture and stirred for about 30 minutes. The pH of the reaction mixture is adjusted to 7.0 to 7.5 with sodium bicarbonate (135 g). The reaction mixture is stirred for 30-40 minutes. The solid obtained is filtered, washed with water (500 mL) and suction dried. The product obtained is dissolved in dichloromethane (1000 mL) and treated with anhydrous sodium sulfate (50 g). The contents were filtered and distilled completely under reduced pressure below 400° C. to give 5-androsten-3,17-dione.

Yield: 83%

Example 4

Preparation of Dehydroepiandrosterone (DHEA)

In a 50 mL reactor with overhead stirring, 5-Androsten-3,17-dione (1.80 g) in methyltetrahydrofuran (20 mL) is added to mixture of potassium phosphate buffer solution (10 mL, having ionic strength of 50 mM, pH 6.5) containing $NAD^+$ (0.1 mg/mL), $NADP^+$ (0.1 mg/mL), $MgCl_2$ hexahydrate (2 mM, 0.4 mg/mL), glucose (100 mM, 18.75 mg/mL), glucose dehydrogenase GDH CDX-901 (0.1 mg/mL) and enzyme of Sequence ID No:1 (54 mg, 3% wt/wt). The reaction mass is stirred at about 30-35° C. at 1000 rpm. The pH of the reaction mass is maintained at about 6.5 using sodium bicarbonate and maintained at about 30-35° C. at 1000 rpm for about 4 hours to about 24 hours. The organic layer is separated. The aqueous layer is extracted with ethyl acetate (50 mL). Combined organic layers are dried over MgSO4 and evaporated to dryness to give crude dehydroepiandrosterone (1.86 g) of 94.5% purity by quantitative NMR and it was used in the next step without further purification. $^1H$ NMR ($CDCl_3$, 400 mHz) δ 5.38 (d, 1H), 3.50-3.58 (m, 1H), 2.47 (dd, 1H), 2.22-2.39 (m, 2H), 2.04-2.12 (m, 2H), 1.92-1.98 (m, 1H), 1.83-1.89 (m, 3H), 1.44-1.71 (m, 6H), 1.22-1.29 (m, 2H), 0.97-1.14 (m, 2H), 1.04 (s, 3H), 0.89 (s, 3H).

Example 5

Preparation of Dehydroepiandrosterone (DHEA)

In a 100 mL reactor with overhead stirring, 5-Androsten-3,17-dione (3.59 g) in methyltetrahydrofuran (36 mL) is added to mixture of potassium phosphate buffer solution (18 mL, having ionic strength of 50 mM, pH 6.5), containing $NAD^+$ (0.044 mg/mL), NADP+ (0.044 mg/mL), $MgCl_2$ hexahydrate (5 mM, 1.67 mg/mL), glucose (100 mM, 18.44 mg/mL), glucose dehydrogenase GDH CDX-901 (0.26 mg/mL) and Sequence ID No:1 (100 mg, 2.8% wt/wt). The reaction mass is stirred at about 20-32° C. at 1000 rpm. The pH of the reaction mass is maintained at about 6.5 using sodium bicarbonate and maintained at about 20-32° C. at 1000 rpm for about 4 hours to about 24 hours. Methyltetrahydrofuran layer is evaporated under vacuum and the precipitated product is isolated by filtration and washed twice with 50 mL of water, and then dried under vaccum to give 3.47 g of crude product of 79% potency by quantitative NMR. 0.50 g of the obtained crude product is re-crystallized from ethyl acetate/heptane to give dehydroepiandrosterone.

Yield: 0.35 g

Purity: >98%.

Example 6

Preparation of Dehydroepiandrosterone Acetate (DHEA Acetate)

Dehydroepiandrosterone (10 g, 35 mmol) and pyridine (25 ml) are charged into a round bottom flask at 25-30° C.

Acetic anhydride (26 mL, 277 mmol) is added dropwise to the above reaction mixture and stirred at room temperature under argon atmosphere for about 12 hours. Ice water (20 mL) is poured into the reaction mixture. The white precipitate formed is dissolved in dichloromethane (200 mL) and the organic layer is washed with 1M hydrochloric acid (3.20 mL), 5% sodium bicarbonate (1.30 mL), brine solution (1.30 mL) and water (1.30 mL), dried over anhydrous sodium sulfate and evaporated under reduced pressure to give crude dehydroepiandrosterone acetate. The obtained crude dehydroepiandrosterone acetate is recrystallized from acetone to give dehydroepiandrosterone acetate.

Yield: 10.9 g
Purity: 95%

Example 7

Preparation of Dehydroepiandrosterone Acetate (DHEA Acetate)

Crude dehydroepiandrosterone (2.21 g, 7.68 mmol) and toluene (25 ml) are charged into a round bottom flask at 25-30° C. 4-Dimethylaminopyridine (66 mg), acetic anhydride (1.45 mL, 1.57 g, 15.36 mmol) and triethylamine (2.33 g, 3.2 mL, 23.0 mmol) are charged into above solution and stirred at room temperature for about 3 hours. The obtained reaction mass is quenched with 1M HCl (30 mL) and the organic layer is washed with water (30 mL), sodium bicarbonate solution (30 mL), dried over magnesium sulphate and concentrated under vacuum to give dehydroepiandrosterone acetate.

Yield: 85%
Purity by HPLC: 84.2%

---

We claim:

1. A process for preparing 3β-hydroxyandrost-5-en-17-one of formula (I)

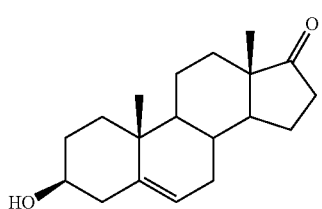
(I)

comprising reducing 3-oxo group of Δ⁵-androstene-3,17-dione of formula (II)

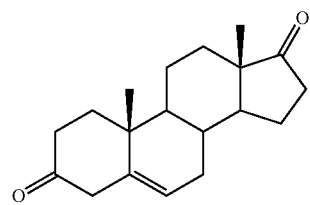
(II)

using a ketoreductase enzyme having SEQ ID NO:1.

2. A process for preparing the compound of formula (III)

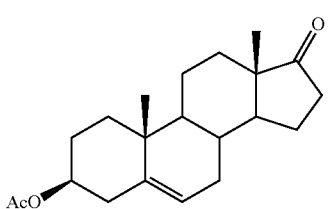
(III)

comprising:
acetylating the compound of formula (I), wherein the compound of formula (I) is prepared according to claim 1,

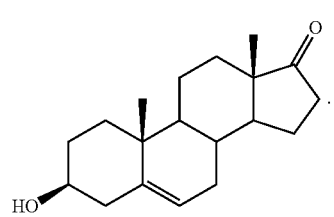
(I)

3. A process for the preparing compound of formula (III)

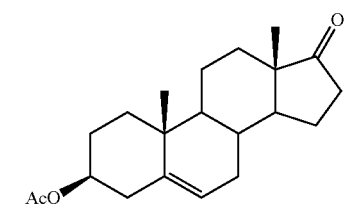
(III)

comprising the steps of:
a) isomerizing Δ⁴-androstene-3,17-dione of formula (IV)

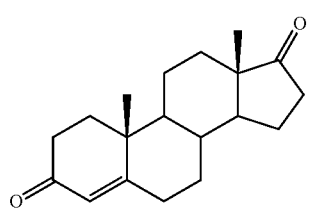
(IV)

to give Δ⁵-androstene-3,17-dione of formula (II);

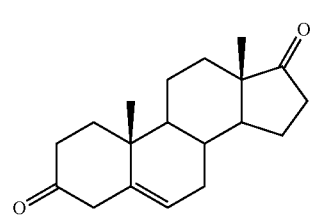
(II)

b) regioselectively and stereoselectively reducing the 3-oxo group of Δ⁵-androstene-3,17-dione of formula (II) using a ketoreductase enzyme, wherein the compound of formula (II) is prepared according to claim 1 to obtain 3β-hydroxyandrost-5-en-17-one of formula (I); and

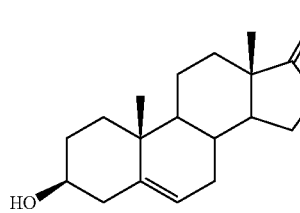
(I)

c) acetylating the compound of formula (I) to obtain the compound of formula (III).

4. The process of claim 1, wherein compound of formula (I) is converted to Abiraterone acetate.

5. The process of claim 1, wherein the compound of formula (I) is converted to DHEA Enanthate.

* * * * *

SEQUENCE LISTING

```
<160> NUMBER OF SEQ ID NOS: 1

<210> SEQ ID NO 1
<211> LENGTH: 264
<212> TYPE: PRT
<213> ORGANISM: Sphingomonas wittichii

<400> SEQUENCE: 1

Met Ala Arg Leu Ala Gly Lys Val Ala Ile Ile Ser Gly Ala Ala Gln
1               5                   10                  15

Gly Met Gly Ala Ala Thr Ala Arg Leu Phe Ala Ala Glu Gly Ala Lys
            20                  25                  30

Val Val Ile Gly Asp Val Leu Asp Glu Lys Gly Arg Ala Val Ala Ala
        35                  40                  45

Glu Leu Gly Ala Asp Val Ala Leu Tyr Gln His Leu Asp Val Arg Glu
    50                  55                  60

Glu Glu Gln Trp Ala Ala Ile Val Lys Ala Ala Val Asp Arg Phe Gly
65                  70                  75                  80

Lys Leu Asp Ile Leu Val Asn Asn Ala Ala Val Thr His Phe Gly Ala
                85                  90                  95

Ser Glu Glu Leu Arg Lys Glu Asp Ala Glu Arg Val Leu Gly Ile Asn
            100                 105                 110

Leu Ile Gly Thr Met Met Gly Val Lys His Ala Val Pro Ala Leu Lys
        115                 120                 125

Ala Asn Gly Arg Gly Val Ile Val Asn Ile Ser Ser Val Asp Gly Leu
    130                 135                 140

Arg Gly Cys Asn Gly Leu Val Ala Tyr Thr Ala Ser Lys Trp Ala Val
145                 150                 155                 160

Arg Gly Ile Thr Lys Ser Tyr Ala Tyr Glu Phe Gly Pro Leu Gly Ile
                165                 170                 175

Arg Val Val Ser Ile His Pro Gly Gly Val Asn Thr Glu Met Gly Asn
            180                 185                 190

Pro Gly His Glu Ser Val Glu Thr Val Asn Ala Arg Ser Phe Gly Arg
        195                 200                 205

Val Pro Leu Gln Arg Ile Gly Glu Pro Glu Glu Ile Ala Arg Ala Thr
    210                 215                 220
```

```
Leu Phe Val Cys Ser Asp Glu Ala Ser Tyr Ile Ser Gly Ala Glu Ile
225                 230                 235                 240

Ala Val Asp Gly Gly Trp Thr Ala Gly His Tyr Glu Pro Ala Leu Pro
                245                 250                 255

Gly Cys Pro Asp His Leu Arg Gly
                260
```